United States Patent
Meyer-Böhm et al.

(10) Patent No.: US 8,790,703 B2
(45) Date of Patent: Jul. 29, 2014

(54) METHOD FOR PRODUCING PREPARATIONS OF SUBSTANCES POORLY SOLUBLE IN WATER

(75) Inventors: Kathrin Meyer-Böhm, Feucht (DE); Rainer Dobrawa, Stuttgart (DE); Stefan Fischer, Freinsheim (DE); Karl Kolter, Limburgerhof (DE)

(73) Assignee: BASF SE, Ludwigshafen (DE)

( * ) Notice: Subject to any disclaimer, the term of this patent is extended or adjusted under 35 U.S.C. 154(b) by 0 days.

(21) Appl. No.: 13/262,380

(22) PCT Filed: Mar. 30, 2010

(86) PCT No.: PCT/EP2010/054167
§ 371 (c)(1),
(2), (4) Date: Sep. 30, 2011

(87) PCT Pub. No.: WO2010/112489
PCT Pub. Date: Oct. 7, 2010

(65) Prior Publication Data
US 2012/0022079 A1    Jan. 26, 2012

(30) Foreign Application Priority Data
Mar. 31, 2009 (EP) .................. 09156892

(51) Int. Cl.
| | | |
|---|---|---|
| *A61K 9/14* | (2006.01) | |
| *C08F 283/06* | (2006.01) | |
| *C08F 18/08* | (2006.01) | |
| *C08F 226/06* | (2006.01) | |
| *C08F 226/10* | (2006.01) | |
| *A61K 8/91* | (2006.01) | |
| *A61K 9/20* | (2006.01) | |
| *A23L 1/29* | (2006.01) | |
| *A23L 1/27* | (2006.01) | |
| *A23L 1/30* | (2006.01) | |
| *A61K 47/34* | (2006.01) | |
| *A61K 8/86* | (2006.01) | |
| *A61K 9/16* | (2006.01) | |

(52) U.S. Cl.
CPC ............ *A61K 9/2095* (2013.01); *C08F 283/06* (2013.01); *C08F 18/08* (2013.01); *C08F 226/06* (2013.01); *C08F 226/10* (2013.01); *A61K 8/91* (2013.01); *A23L 1/29* (2013.01); *A23L 1/27* (2013.01); *A23L 1/30* (2013.01); *A61K 47/34* (2013.01); *A61K 8/86* (2013.01); *A61K 9/146* (2013.01); *A61K 9/1641* (2013.01); *A61K 9/1682* (2013.01); *A61K 9/1694* (2013.01)
USPC ...... 424/489; 514/254.07; 514/356; 514/396; 514/545; 514/255.04

(58) Field of Classification Search
CPC ...... C08F 283/06; C08F 18/08; C08F 226/06; C08F 226/10

USPC ............... 514/254.07, 356, 396, 545, 255.04; 264/128; 424/489, 497
See application file for complete search history.

(56) References Cited

U.S. PATENT DOCUMENTS

| | | | |
|---|---|---|---|
| 6,271,307 B1 | 8/2001 | Huff et al. | |
| 6,867,262 B1 | 3/2005 | Angel et al. | |
| 2008/0274194 A1* | 11/2008 | Miller et al. | ................ 424/489 |
| 2008/0293828 A1* | 11/2008 | Bouillo et al. | ............ 514/772.3 |
| 2009/0036551 A1 | 2/2009 | Venkatesh et al. | |
| 2010/0204425 A1* | 8/2010 | Mertoglu et al. | ............ 526/264 |
| 2010/0280047 A1 | 11/2010 | Kolter et al. | |
| 2011/0178183 A1 | 7/2011 | Meyer-Boehm et al. | |
| 2011/0195118 A1 | 8/2011 | Kolter et al. | |

FOREIGN PATENT DOCUMENTS

| | | |
|---|---|---|
| DE | 19935063 | 2/2001 |
| EP | 0953347 | 11/1999 |
| EP | 2158922 | 3/2010 |
| WO | WO-2007/051743 | 5/2007 |
| WO | WO-2009/013202 | 1/2009 |
| WO | WO-2010/034688 | 4/2010 |
| WO | WO-2010/072573 | 7/2010 |
| WO | WO-2010/112489 | 10/2010 |

OTHER PUBLICATIONS

Prodduturi et al. (Water Vapor Sorption of Hot-Melt Extruded Hydroxypropyl Cellulose Films: Effect on Physico-Mechanical Properties, Release Characteristics, and Stability, Journal of Pharmaceutical Sciences (Dec. 2004) 93 (12): 3047-3056 [Retrieved from internet <URL: http://onlinelibrary.wiley.com/doi/10.1002/jps.20222/pdf >]), 10 pages.*
International Preliminary Report on Patentability for PCT/EP2010/054167 (WIPO, Nov. 1, 2011), 8 pages.*

(Continued)

*Primary Examiner* — Jason Sims
*Assistant Examiner* — Miriam A Levin
(74) *Attorney, Agent, or Firm* — Servilla Whitney LLC

(57) ABSTRACT

The invention relates to a process for producing formulations of sparingly water-soluble substances, said sparingly soluble substances being present in amorphous embedded form in a copolymer, and said copolymer being obtained by free-radically initiated polymerization of a mixture of i) 30 to 80% by weight of N-vinyllactam, ii) 10 to 50% by weight of vinyl acetate, and iii) 10 to 50% by weight of a polyether, with the proviso that the sum of components i), ii) and iii) equals 100% by weight, which comprises embedding the sparingly soluble substance into the copolymer at temperatures above the melting point of the sparingly soluble substances.

17 Claims, No Drawings

(56) References Cited

OTHER PUBLICATIONS

Prodduturi et al, Water Vapor Sorption of Hot-Melt Extruded Hydroxypropyl Cellulose Films: Effect on Physico-Mechanical Properties, Release Characteristics, and Stability, Journal of Pharmaceutical Sciences (Dec. 2004), 93(12):3047-3056 (10 pages).*

Fax to Michelle Cristaldi with Prodduturi et al. article (cited above) as attachment. (Nov. 6, 2012), (11 pages).*

Liu et al. (Use of polymer combinations in the preparation of solid dispersions of a thermally unstable drug by hot-melt extrusion, Acta Pharmaceutica Sinica B (2013) 3(4): 263-272), 12 pages.*

Chokshi et al. (Characterization of Physico-Mechanical Properties of Indomethacin and Polymers to Assess their Suitability for Hot-Melt Extrusion Process as a Means to Manufacture Solid Dispersion/Solution, Journal of Pharmaceutical Sciences (Nov. 2005) 94 (11): 2463-2474), 12 pages.*

"Machine Translation of EP2158922", Mar. 3, 2010, 7 pages.
"Machine Translation of WO2010/072573", Jul. 1, 2010, 12 pages.
"Machine Translation of WO2010/112489", Oct. 7, 2010, 11 pages.
"PCT International Search Report for PCT/EP2010/054167", Dec. 8, 2010, 3 pages.

* cited by examiner

METHOD FOR PRODUCING PREPARATIONS OF SUBSTANCES POORLY SOLUBLE IN WATER

CROSS-REFERENCE TO RELATED APPLICATIONS

This application is the national stage entry of PCT/EP2010/054167, filed on Mar. 30, 2010, which claims priority to European Patent application number 09156892.3, filed on Mar. 31, 2009, both of which are incorporated herein by reference in their entireties.

BACKGROUND

In the production of homogeneous formulations, especially of biologically active substances, the solubilization of hydrophobic, i.e. sparingly water-soluble, substances has gained very great practical significance.

Solubilization is understood to mean the solubilizing of substances which are sparingly soluble or insoluble in a particular solvent, especially water, by interface-active compounds, the solubilizers. Such solubilizers are capable of converting sparingly water-soluble or water-insoluble substances to clear, at most opalescent aqueous solutions, without the chemical structure of these substances undergoing any change in the process (cf. Römpp Chemie Lexikon, 9th edition, vol. 5, p. 4203, Thieme Verlag, Stuttgart, 1992).

In the solubilizates produced, the sparingly water-soluble or water-insoluble substance is present in colloidally dissolved form in the molecular associates of the surface-active compounds which form in aqueous solution, for example, hydrophobic domains or micelles. The resulting solutions are stable or metastable monophasic systems with a visually clear to opalescent appearance.

Solubilizers can, for example, improve the appearance of cosmetic formulations and of food formulations by making the formulations transparent. Moreover, in the case of pharmaceutical formulations, the bioavailability and hence the efficacy of medicaments can be enhanced by the use of solubilizers.

A further desirable requirement on solubilizers is the ability to form so-called "solid solutions" with sparingly soluble substances. The term "solid solution" describes a state in which a substance is distributed in colloidal dispersion or ideally molecular dispersion in a solid matrix, for example, a polymer matrix. Such solid solutions lead, for example, when used in solid pharmaceutical administration forms of a sparingly soluble active ingredient, to improved release of the active ingredient. An important requirement on such solid solutions is that they are stable over a long period even in the course of storage, which means that the active ingredient does not crystallize out. Moreover, the capacity of the solid solution or, in other words, the ability to form stable solid solutions with maximum active ingredient contents is also of significance.

In the formation of solid solutions, in addition to the basic ability of the solubilizers to form solid solutions, the hygroscopicity of the solubilizers also plays an important role. Solubilizers which absorb too much water from the ambient air lead to deliquescence of the solid solution and the undesired crystallization of the active ingredients. In the course of processing to administration forms too, too great a hygroscopicity may present problems.

Many known polymeric solubilizers have the disadvantages that they do not form stable solid solutions. Moreover, they still leave room for improvement as far as solubilization in aqueous systems is concerned. With regard to processability too, some of the known solubilizers, owing to their tendency to tackiness, have disadvantages since they are not sufficiently free-flowing powders.

DE-A 199 350 63 discloses polyalkylene oxide-containing graft polymers, based on vinyllactams and vinyl acetate, and the use thereof as gas hydrate inhibitors.

EP-A 953 347 discloses the use of polyalkylene oxide-containing graft polymers as solubilizers. The graft polymers of vinyl acetate and polyalkylene oxides described there are frequently not a powder, but instead glutinous liquids, which is disadvantageous in application terms.

WO 2007/051743 discloses the use of water-soluble or water-dispersible copolymers of N-vinyllactam, vinyl acetate and polyethers as solubilizers for pharmaceutical, cosmetic, food technology, agrochemical or other industrial applications. It is described in quite general terms therein that the corresponding graft polymers can also be processed with the active ingredients in the melt.

WO 2009/013202 discloses that such graft polymers of N-vinyllactam, vinyl acetate and polyethers can be melted in an extruder and mixed with pulverulent or liquid active ingredients, the extrusion being described at temperatures significantly below the melting point of the active ingredients.

However, mixing of the molten graft polymer with pulverulent or liquid active ingredients cannot achieve satisfactorily high and simultaneously stable active ingredient loading. In particular, the achievement of a stable X-ray-amorphous state of the active ingredient is not always possible to a satisfactory degree.

SUMMARY

Embodiments of the present invention relate to a processes for producing formulations of sparingly water-soluble substances by embedding the sparingly soluble substances into copolymers, which are obtained by polymerizing vinyl acetate and N-vinyllactams in the presence of a polyether. The embedding can be effected by extrusion and at temperatures above the melting point of the sparingly water-soluble substances, the substances being present in amorphous form in the extruded formulation.

The corresponding copolymers are suitable as solubilizers for sparingly water-soluble substances.

DETAILED DESCRIPTION

In accordance with one or more embodiments, provided is a process for incorporating sparingly water-soluble substances into a formulation with improved solubility.

Accordingly, a process has been found for producing formulations of sparingly water-soluble substances, said sparingly soluble substances being present in amorphous embedded form in a copolymer, and said copolymer being obtained by free-radically initiated polymerization of a mixture of i) 30 to 80% by weight of N-vinyllactam,
ii) 10 to 50% by weight of vinyl acetate, and
iii) 10 to 50% by weight of a polyether, with the proviso that the sum of components i), ii) and iii) equals 100% by weight, which comprises the embedding at temperatures above the melting point of the biologically active substances.

In one embodiment of the invention, preferred polymers obtained from:

i) 30 to 70% by weight of N-vinyllactam,
ii) 15 to 35% by weight of vinyl acetate, and
iii) 10 to 35% by weight of a polyether, are used.

Polymers used with particular preference are obtainable from:
i) 40 to 60% by weight of N-vinyllactam,
ii) 15 to 35% by weight of vinyl acetate, and
iii) 10 to 30% by weight of a polyether.

Polymers for use with very particular preference are obtainable from
i) 50 to 60% by weight of N-vinyllactam,
ii) 25 to 35% by weight of vinyl acetate, and
iii) 10 to 20% by weight of a polyether.

For the preferred and particularly preferred compositions too, the proviso applies that the sum of components i), ii), and iii) equals 100% by weight.

Useful N-vinyllactam includes N-vinylcaprolactam or N-vinylpyrrolidone or mixtures thereof. Preference is given to using N-vinylcaprolactam.

The graft bases used are polyethers. Useful polyethers are preferably polyalkylene glycols. The polyalkylene glycols may have molecular weights of 1000 to 100 000 Da [daltons], preferably 1500 to 35 000 Da, more preferably 1500 to 10 000 Da.

The molecular weights are determined proceeding from the OH number measured to DIN 53240.

Particularly preferred polyalkylene glycols include polyethylene glycols. Also additionally suitable are polypropylene glycols, polytetrahydrofurans or polybutylene glycols, which are obtained from 2-ethyloxirane or 2,3-dimethyloxirane.

Suitable polyethers are also random or block copolymers of polyalkylene glycols obtained from ethylene oxide, propylene oxide and butylene oxides, for example polyethylene glycol-polypropylene glycol block copolymers. The block copolymers may be of the AB type or of the ABA type.

The preferred polyalkylene glycols also include those which are alkylated at one or both OH end groups. Useful alkyl radicals include branched or unbranched $C_1$- to $C_{22}$-alkyl radicals, preferably $C_1$-$C_{18}$-alkyl radicals, for example, methyl, ethyl, n-butyl, isobutyl, pentyl, hexyl, octyl, nonyl, decyl, dodecyl, tridecyl or octadecyl radicals.

General processes for preparing the inventive graft copolymers are known per se. They are prepared by free-radically initiated polymerization, preferably in solution, in nonaqueous organic solvents or in mixed nonaqueous/aqueous solvents. Suitable preparation processes are described, for example, in WO 2007/051743 and WO 2009/013202, the disclosure of which is referred to explicitly with regard to the preparation process.

The embedding is preferably effected by melt extrusion.

The copolymers can be supplied to the extruder either in pulverulent form or in the form of solutions or dispersions.

The dispersions or solutions of the polymer can be converted to solid form by removing the dispersant or solvent in the extruder in the molten state and cooling the melt.

The melt thus obtained can then be cooled and granulated. Since the polymer is generally water-soluble, the customary methods of granulation of thermoplastic melts by cooling by means of water are less of an option. Alternatives are so-called hot-cutting or cooling under air or protective gas, for example, on a Teflon or chain belt and subsequent granulation of the cooled melt extrudate.

The following methods A-E can be used in principle:

| | |
|---|---|
| A | Physical powder mixing of polymer and active ingredient, and supply of this powder mixture in the extruder |
| B | Supply of the active ingredient via a separate bypass into the unmolten polymer |
| C | Supply of the active ingredient via a side feed into the molten polymer (polymer extruded in pulverulent form) |
| D | Polymer solution with water or ethyl acetate with active ingredient dispersed therein in partly degassed polymer melt; polymer extruded from solution |
| E | Supply of the active ingredient via a side feed into the molten polymer |

For the process according to the invention, suitable extruder types in principle are the customary extruder types known to those skilled in the art. Typically, these comprise a housing, a drive unit with transmission, and a process unit which consists of the extruder shaft or shafts equipped with the screw elements, modular construction being assumed in this case.

The extruder consists of a plurality of sections, which are each assigned to particular process units. Each of these sections consists of one or more barrels (barrel blocks) as the smallest independent unit and the corresponding screw sections with the screw elements corresponding to the process task.

The individual barrels should be heatable. In addition, the barrels may also be designed for cooling, for example, for cooling with water. The individual barrel blocks are preferably independently heatable and coolable, such that different temperature zones can also be established along the extrusion direction.

The extruder is advantageously configured as a corotatory twin screw extruder. The screw configuration may have different shear levels according to the product. Kneading elements must be used especially in the melting zone. It is also possible to use reverse kneading elements.

Suitable twin screw extruders may have a screw diameter of 16 to 70 mm and a length of 25 to 40 D.

The entire extruder is formed from barrel blocks, whose temperatures can be controlled individually. The first two barrels may be temperature-controlled for the purpose of better material intake. From the third barrel, a constant temperature is preferably established, which should be selected specifically to the material and depends especially on the melting point of the active ingredient used and the glass transition temperature of the polymer. The resulting product temperature typically, however, depends on the shear level of the screw element used and may in some cases be 20-30° C. higher than the barrel temperature.

The melting zone may be followed downstream by a venting zone, which is advantageously operated at ambient pressure.

The round dies used may have a diameter of 0.5 to 5 mm. Other die forms such as slot dies may likewise be used, in particular when a greater material throughput is desired.

The two corotatory screws are designed such that, downstream of an intake zone consisting of conveying elements, kneading blocks with a downstream flow restrictor are already used in the third heating zone. After a short decompression zone composed of conveying elements, the now molten material is mixed again in a kneading zone. This is followed by a conveying element zone with downstream kneading elements. There follows a conveying element zone with downstream kneading zone. Finally, the discharge of the material is ensured with a conveying element zone.

The resulting extrudates can be processed with a granulator to pellets which can in turn be comminuted (ground) further to a powder. The pellets or powder can be filled into capsules or pressed to tablets using customary tableting assistants.

In addition, it is possible to use, during the extrusion, water, organic solvents, buffer substances or plasticizers. Especially water or volatile alcohols are options for this purpose. This process enables reaction at relatively low temperature. The amounts of solvent or plasticizer are typically between 0 and 30% of the extrudable material. The water or solvent can already be removed by a venting point in the extruder at standard pressure, or by applying reduced pressure. Alternatively, these components evaporate when the extrudate leaves the extruder and the pressure is reduced to standard pressure. In the case of nonvolatile components, the extrudate can correspondingly be dried subsequently.

In a particular variant of the production process, directly after the extrusion, the thermoplastic material is calendered to a tablet-like compact which constitutes the ultimate administration form. In this variant, it may be advisable to add further constituents, for example polymers for adjusting the glass transition temperature and the melt viscosity, disintegrants, solubilizers, plasticizers, dyes, flavorings, sweeteners, etc. actually before or during the extrusion. In principle, these substances can also be used when the extrudate is first comminuted and then pressed to tablets.

The addition of crystallization-inhibiting substances, for example, Kollidon 30 allows the stability of the solid solutions to be increased.

In addition, it is also additionally possible to incorporate surfactants which lower the melt viscosity and hence the extrusion temperature into the formulations. These substances may also positively influence the possible crystallization. Suitable substances are, for example, Solutol® HS 15, Tween® 80, Cremophor RH40, docusate sodium or sodium laurylsulfate.

The still plastic mixture is preferably extruded through a die, cooled and comminuted. Suitable comminution methods are in principle all known techniques customary therefor, such as hot or cold cuffing.

The extrudate is cut, for example, with rotating blades or with an air jet and then cooled with air or under protective gas.

It is also possible to lay the extrudate as a melt strand on a cooled belt (stainless steel, Teflon, chain belt) and to granulate it after solidification.

Subsequently, the extrudate can optionally be ground. The formulations are obtained as free-flowing water-soluble powders. Preference is given to establishing particle sizes of 20 to 250 µm.

In addition, it is also possible to process the plastic mixture of polymer and active substance by injection molding.

The formulations obtained by the process according to the invention can in principle be used in all fields in which only sparingly water-soluble or water-insoluble substances are either to be used in aqueous formulations or are to display their action in an aqueous medium.

According to the invention, the term "sparingly water-soluble" also comprises virtually insoluble substances and means that, for a solution of the substance in water at 20° C. at least 30 to 100 g of water is required per g of substance. In the case of virtually insoluble substances, at least 10 000 g of water are required per g of substance.

In the context of the present invention, sparingly-water soluble substances are preferably understood to mean biologically active substances such as active pharmaceutical ingredients for humans and animals, active cosmetic or agrochemical ingredients, or food supplements or active dietetic ingredients.

In addition, useful sparingly soluble substances to be solubilized also include dyes such as inorganic or organic pigments.

According to the invention, useful biologically active substances include, in principle, all solid active ingredients which have a melting point below the decomposition point under extrusion conditions of the copolymers. The copolymers can generally be extruded at temperatures up to 260° C. The lower temperature limit is guided by the composition of the mixtures to be extruded and the sparingly soluble substances to be processed in each case.

The active pharmaceutical ingredients used are water-insoluble substances or substances with low water solubility. According to DAB 9 (Deutsches Arzneimittelbuch, German Pharmacopeia), the solubility of active pharmaceutical ingredients is classified as follows: low solubility (soluble in 30 to 100 parts of solvent); sparingly soluble (soluble in 100 to 1000 parts of solvent); virtually insoluble (soluble in more than 10 000 parts of solvent). The active ingredients may come from any indication sector.

Examples here include benzodiazepines, antihypertensives, vitamins, cytostatics—especially taxol, anesthetics, neuroleptics, antidepressives, antivirals, for example anti-HIV drugs, antibiotics, antimycotics, antidementives, fungicides, chemotherapeutics, urologics, thrombocyte aggregation inhibitors, sulfonamides, spasmolytics, hormones, immunoglobulins, sera, thyroid therapeutics, psychopharmaceuticals, Parkinson's drugs and other antihyperkinetics, ophthalmics, neuropathy preparations, calcium metabolism regulators, muscle relaxants, anesthetics, lipid-lowering drugs, liver therapeutics, coronary drugs, cardiac drugs, immunotherapeutics, regulatory peptides and inhibitors thereof, hypnotics, sedatives, gynaecologicals, gout remedies, fibrinolytics, enzyme preparations and transport proteins, enzyme inhibitors, emetics, blood-flow stimulators, diuretics, diagnostics, corticoids, cholinergics, biliary therapeutics, antiasthmatics, bronchodilators, beta-receptor blockers, calcium antagonists, ACE inhibitors, arteriosclerotic drugs, anti-inflammation drugs, anticoagulants, antihypotensives, antihypoglycemics, antihypertensives, antifibrinolytics, antiepileptics, antiemetics, antidotes, antidiabetics, antiarrhythmics, antianemics, antiallergics, anthelmintics, analgesics, analeptics, aldosterone antagonists, slimming drugs.

Among the abovementioned pharmaceutical formulations, particular preference is given to those which are orally administrable formulations.

The content of inventive solubilizer in the pharmaceutical formulation is, depending on the active ingredient, in the range from 1 to 75% by weight, preferably 5 to 60% by weight, more preferably 5 to 50% by weight.

A further particularly preferred embodiment relates to pharmaceutical formulations in which the active ingredients and the copolymer are present as a solid solution. In this case, the removal of the solvent and the incorporation of the active substance can be effected in one process step. The weight ratio of copolymer to active ingredient here is preferably from 1:1 to 4:1, but may be up to 100:1, especially up to 15:1. The only factors are that, when used in the finished drug form, a sufficient amount of active ingredient is firstly present in the drug form, and the forms secondly do not become too large in the case of oral drug forms.

To produce pharmaceutical administration forms, for example, tablets, the extrudates can be admixed with customary pharmaceutical excipients.

These are substances form the class of the fillers, plasticizers, solubilizers, binders, silicates and disintegrants and adsorbents, lubricants, flow agents, dyes, stabilizers such as antioxidants, wetting agents, preservatives, mold release agents, aromas or sweeteners, preferably fillers, plasticizers and solubilizers.

The fillers added may, for example, be inorganic solids such as oxides of magnesium, aluminum, silicon, titanium carbonate or calcium carbonate, calcium phosphate or magnesium phosphate or organic fillers such as lactose, sucrose, sorbitol, mannitol.

Suitable plasticizers are, for example, triacetin, triethyl citrate, glyceryl monostearate, low molecular weight polyethylene glycols or poloxamers.

Suitable additional solubilizers are interface-active substances with an HLB (Hydrophilic Lipophilic Balance) value greater than 11, for example hydrogenated castor oil ethoxylated with 40 ethylene oxide units (Cremophor® RH 40), castor oil ethoxylated with 35 ethylene oxide units (Cremophor EL), Polysorbate 80, poloxamers or sodium laurylsulfate.

The lubricants used may be stearates of aluminum, calcium, magnesium and tin, and also magnesium silicate, silicones and the like.

The flow agents used may, for example, be talc or colloidal silicon dioxides.

A suitable binder is, for example, microcrystalline cellulose.

The disintegrants may be crosslinked polyvinylpyrrolidone or crosslinked sodium carboxymethyl starch. Stabilizers may be ascorbic acid or tocopherol.

Dyes are, for example, iron oxides, titanium dioxide, triphenylmethane dyes, azo dyes, quinoline dyes, indigotin dyes, carotenoids, in order to dye the administration forms, opacifiers, such as titanium dioxide or talc, in order to increase the transparency and to save dyes.

In addition to use in cosmetics and pharmacy, the formulations produced in accordance with the invention are also suitable for use in the foods sector, for example, for the incorporation of sparingly water-soluble or water-insoluble nutrients, assistants or additives, for example, fat-soluble vitamins or carotenoids. Examples include drinks, colored with carotenoids.

The use of the formulations obtained in accordance with the invention in agrochemistry may include formulations which comprise pesticides, herbicides, fungicides or insecticides, and in particular also those formulations of crop protection compositions which are used as formulations for spraying or watering.

With the aid of the process according to the invention, it is possible to obtain so-called solid solutions comprising sparingly soluble substances. Solid solutions refer in accordance with the invention to systems in which no crystalline components of the sparingly soluble substance are observed.

On visual assessment of the stable solid solutions, no amorphous constituents are evident. The visual assessment can be effected with a light microscope either with or without a polarization filter at 40-fold magnification.

In addition, the formulations can also be examined for crystallinity or amorphicity with the aid of XRD (X-ray diffraction) and DSC (differential scanning calorimetry).

The formulations obtained by the process according to the invention are, as stated, present in amorphous form which means that the crystalline components of the biologically active substance are less than 5% by weight. The amorphous state is preferably checked by means of DSC or XRD. Such an amorphous state can also be referred to as an X-ray amorphous state.

The process according to the invention allows the production of stable formulations with a high active ingredient loading and good stability with regard to the amorphous state of the sparingly soluble substance.

EXAMPLES

Preparation of the Polymer

In a stirred apparatus, the initial charge without the portion from feed 2 was heated to 77° C. under an $N_2$ atmosphere. When the internal temperature of 77° C. had been attained the portion from feed 2 was added and partly polymerized for 15 min. Subsequently, feed 1 was metered in within 5 h and feed 2 within 2 h. Once all feeds had been metered in, the reaction mixture was polymerized for a further 3 h. After the further polymerization, the solution was adjusted to a solids content of 50% by weight.

Initial charge: 25 g of ethyl acetate
    104.0 g PEG 6000,
    1.0 g of feed 2
Feed 1: 240 g of vinyl acetate
Feed 2: 456 g of vinylcaprolactam
    240 g of ethyl acetate
Feed 3: 10.44 g of tert-butyl perpivalate (75% by weight in aliphatics mixture)
    67.90 g of ethyl acetate Subsequently, the solvent was removed by a spray process to obtain a pulverulent product. The K value was 36, measured in 1% by weight solution in ethanol.

The twin screw extruder which was used for the production of the formulations described in the examples which follow had a screw diameter of 16 mm and a length of 40 D. The entire extruder was formed from 8 individually temperature-controllable barrel blocks. For the purpose of better material intake, the temperatures of the first two barrels were controlled at 20° C. and at 70° C. respectively. From the third barrel, a constant temperature was established.

The solid solutions produced were examined by means of XRD and DSC for crystallinity and amorphicity using the following equipment and conditions:

XRD
Instrument: D 8 advance diffractometer with 9-tube sample changer (from Bruker/AXS)
Measurement method: θ-θ geometry in reflection
Angle range 2 Theta: 2-80°
Step width: 0.02°
Measurement time per angle step: 4.8 s
Divergence slit: Göbel mirror with 0.4 mm inserted aperture
Antiscattering slit: Soller slit
Detector: Sol-X detector
Temperature: Room temperature
Generator setting: 40 kV/50 mA
DSC
DSC Q 2000 from TA Instruments
Parameters:
Starting weight approx. 8.5 mg
Heating rate: 20K/min
Preparation of Solid Solutions Example 1

1600 g of polymer and 400 g of fenofibrate (melting point 81° C.) were weighed into a Turbula mixing vessel and mixed in the T10B Turbula mixer for 10 minutes.

The mixture was extruded under the following conditions:
Zone temperature from the 3rd cylinder: 130° C.
Screw speed 200 rpm
Throughput 1000 g/h
Die diameter 1 mm
Die pressure: 11 bar
Current consumption: 2.8 A
Power consumption: 0.3 kW
The solid solutions were studied by XRD and by DSC and were found to be amorphous.

Example 2

800 g of polymer and 200 g of cinnarizine (melting point 122° C.) were weighed into a Turbula mixing vessel and mixed in the T10B Turbula mixer for 10 minutes.
The mixture was extruded under the following conditions:
Zone temperature from the 3rd cylinder: 140° C.
Screw speed 200 rpm
Throughput 900 g/h
Die diameter 1 mm
Material temperature: 148° C.
Die pressure: 12 bar
Current consumption: 2.6 A
Power consumption: 0.26 kW
The solid solutions prepared were studied by XRD and by DSC and were found to be amorphous.

Example 3

800 g of polymer and 200 g of ketoconazole (melting point 146° C.) were weighed into a Turbula mixing vessel and mixed in the T10B Turbula mixer for 10 minutes.
The mixture was extruded under the following conditions:
Zone temperature from the 3rd cylinder: 150° C.
Screw speed 200 rpm
Throughput 900 g/h
Die diameter 1 mm
Material temperature: 155° C.
Die pressure: 10 bar
Current consumption: 2.5 A
Power consumption: 0.24 kW
The solid solutions prepared were amorphous according to XRD and DSC.

Example 4

800 g of polymer and 200 g of clotrimazole (melting point 147° C.) were weighed into a Turbula mixing vessel and mixed in the T10B Turbula mixer for 10 minutes.
The mixture was extruded under the following conditions:
Zone temperature from the 3rd cylinder: 150° C.
Screw speed 200 rpm
Throughput 900 g/h
Die diameter 1 mm
Material temperature: 158° C.
Die pressure: 13 bar
Current consumption: 2.9 A
Power consumption: 0.3 kW
The solid solutions prepared were amorphous according to XRD and DSC.

Example 5

800 g of polymer and 200 g of felodipine (melting point 145° C.) were weighed into a Turbula mixing vessel and mixed in the T10B Turbula mixer for 10 minutes.
The mixture was extruded under the following conditions:
Zone temperature from the 3rd cylinder: 150° C.
Screw speed 200 rpm
Throughput 900 g/h
Die diameter 1 mm
Material temperature: 155° C.
Die pressure: 12 bar
Current consumption: 2.6 A
Power consumption: 0.26 kW
The solid solutions prepared were amorphous according to XRD and DSC.

Example 6

1400 g of polymer, 400 g of fenofibrate (melting point 81° C.) and 200 g of Povidon K30 were weighed into a Turbula mixing vessel and mixed in the T10B Turbula mixer for 10 minutes.
The mixture was extruded under the following conditions:
Zone temperature from the 3rd cylinder: 150° C.
Screw speed 200 rpm
Throughput 1000 g/h
Die diameter 1 mm
Die pressure: 14 bar
Current consumption: 3.2 A
Power consumption: 0.35 kW
The solid solutions prepared were amorphous according to XRD and DSC.

Example 7

760 g of polymer, 40 g of sodium laurylsulfate and 200 g of felodipine (melting point 145° C.) were weighed into a Turbula mixing vessel and mixed in the T10B Turbula mixer for 10 minutes.
The mixture was extruded under the following conditions:
Zone temperature from the 3rd cylinder: 160° C.
Screw speed 200 rpm
Throughput 900 g/h
Die diameter 1 mm
Material temperature: 165° C.
Die pressure: 10 bar
Current consumption: 2.4 A
Power consumption: 0.24 kW
The solid solutions prepared were amorphous according to XRD and DSC.

What is claimed is:

1. A process for producing a formulation of a sparingly water-soluble substance, the process comprising amorphously embedding a sparingly water-soluble substance in a graft copolymer, wherein the copolymer is obtained by free-radically initiated polymerization of a mixture of
   i) 30 to 80% by weight of N-vinyllactam,
   ii) 10 to 50% by weight of vinyl acetate, and
   iii) 10 to 50% by weight of a polyether,
with the proviso that the sum of components i), ii) and iii) equals 100% by weight, and wherein embedding the sparingly water-soluble substance into the copolymer occurs at a temperature above the melting point of the sparingly water-soluble substance.

2. The process of claim 1, wherein the copolymer is obtained from
   i) 30 to 70% by weight of N-vinyllactam,
   ii) 15 to 35% by weight of vinyl acetate, and
   iii) 10 to 35% by weight of a polyether.

3. The process of claim 1, wherein the copolymer is obtained using N-vinylpyrrolidone or N-vinylcaprolactam or mixtures thereof as component i).

4. The process of claim 1, wherein the copolymer is obtained using N-vinylcaprolactam as component i).

5. The process of claim 1, wherein the copolymer is obtained using polyethylene glycol as component ii).

6. The process of claim 1, wherein copolymers are obtained using polyethylene glycol as component ii), wherein the polyethylene glycol has a molecular weight of from 1000 daltons to 10 000 daltons.

7. The process of claim 1, wherein the copolymer has a K value of from 10 to 60, as measured in 1% by weight solution in ethanol.

8. The process of claim 7, wherein the copolymer has a K value of from 15 to 40, as measured in 1% by weight solution in ethanol.

9. The process of claim 1, wherein the sparingly water-soluble substance is a biologically active substance.

10. The process of claim 1, wherein the formulation is a pharmaceutical formulation for the treatment of a disease.

11. The process of claim 1, wherein the formulation is a cosmetic formulation.

12. The process of claim 1, wherein the formulation is a food supplement or dietetic agent.

13. The process of claim 1, wherein the formulation is a dye formulation.

14. The process of claim 1, wherein the sparingly water-soluble substance is embedded into the copolymer by melt extrusion.

15. The process of claim 1, wherein the embedding occurs at a temperature of up to 260° C.

16. The process of claim 1, further comprising adding crystallization-inhibiting substances.

17. The process of claim 16, wherein the crystallization-inhibiting substances are surfactants.

* * * * *